United States Patent [19]

Forestier et al.

[11] Patent Number: 4,867,964

[45] Date of Patent: Sep. 19, 1989

[54] COSMETIC COMPOSITION CONTAINING HYDROXYLATED CHALCONE DERIVATIVES AND ITS USE FOR PROTECTING THE SKIN AND THE HAIR AGAINST LUMINOUS RADIATIONS, NEW HYDROXYLATED CHALCONE DERIVATIVES EMPLOYED AND PROCESS FOR THEIR PREPARATION

[75] Inventors: Serge Forestier, Claye-Souilly; Claudine Moire, Romainville; Gerard Lang, Saint-Gratien, all of France

[73] Assignee: L'Oreal, Paris, France

[21] Appl. No.: 133,628

[22] Filed: Dec. 16, 1987

[30] Foreign Application Priority Data

Dec. 16, 1986 [LU] Luxembourg ............... 86715

[51] Int. Cl.$^4$ .......................... A61K 7/42; A61K 7/44; A61K 7/48; A61K 9/12
[52] U.S. Cl. ........................... 424/47; 8/406; 8/408; 424/DIG. 5; 424/59; 424/60; 424/62; 424/63; 424/70; 424/71; 424/72; 514/937; 514/938; 514/943; 514/944
[58] Field of Search ............... 424/59, 60, 47

[56] References Cited

U.S. PATENT DOCUMENTS

| | | | |
|---|---|---|---|
| 3,733,297 | 5/1973 | Buckman et al. | 514/972 |
| 4,279,930 | 7/1981 | Hall et al. | 424/331 |
| 4,584,190 | 4/1986 | Tejima et al. | 424/59 |
| 4,605,674 | 8/1986 | Fujiu et al. | 514/685 |

FOREIGN PATENT DOCUMENTS

| | | | |
|---|---|---|---|
| 0013960 | 8/1980 | European Pat. Off. | 424/331 |
| A69672 | 11/1969 | Fed. Rep. of Germany | 424/59 |
| 1250388 | 10/1971 | United Kingdom | 424/331 |
| 2149789 | 6/1985 | United Kingdom | 424/59 |

OTHER PUBLICATIONS

Journal Med. Chem., vol. 23, No. 3, 1980, pp. 335–338.
J. Chem. Soc. Perkin Trans. 11, 1985, pp. 743–748, Matsushima et al., "Photochemical Cyclization of 2'-Hydroxychalcones".

*Primary Examiner*—Dale R. Ore
*Attorney, Agent, or Firm*—Cushman, Darby & Cushman

[57] ABSTRACT

Cosmetic composition containing hydroxylated chalcone derivatives and its use for protecting the skin and the hair against luminous radiations, new hydroxylated chalcone derivatives employed and process for their preparation.

The invention relates to a cosmetic composition for protecting the skin and the hair against UV rays comprising, in a cosmetically acceptable substrate, at least one derivative of 2-hydroxychalcone of formula:

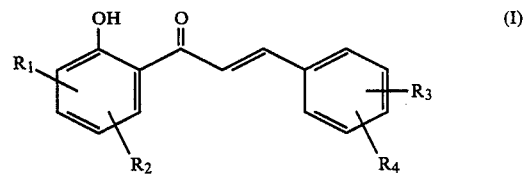

in which $R_1$, $R_2$, $R_3$ and $R_4$ denote, independently of each other, a hydrogen atom, a straight- or branched-chain $C_1$–$C_{12}$ alkyl group, a straight- or branched-chain $C_1$–$C_{12}$ alkyl group or a straight- or branched-chain $C_2$–$C_{20}$ acyloxy group.

The invention also relates to new derivatives of 2-hydroxychalcone and the process for their preparation.

10 Claims, No Drawings

COSMETIC COMPOSITION CONTAINING HYDROXYLATED CHALCONE DERIVATIVES AND ITS USE FOR PROTECTING THE SKIN AND THE HAIR AGAINST LUMINOUS RADIATIONS, NEW HYDROXYLATED CHALCONE DERIVATIVES EMPLOYED AND PROCESS FOR THEIR PREPARATION

The present invention relates to a cosmetic composition containing a hydroxylated chalcone derivative acting as a sunscreen and to its use for protecting the skin and the hair against ultraviolet rays.

It is well known that the skin is sensitive to solar radiations which can cause a mere sunburn or erythema, but also more or less accentuated burns.

However, the solar radiations also have other harmful effects such as a loss of elasticity of the skin and the appearance of wrinkles leading to premature aging. It is also sometimes possible to observe cases of dermatosis.

It is also desirable to provide hair with good protection against photochemical degradation in order to avoid a change in shade, bleaching or a deterioration in the mechanical properties.

It is known, moreover, that the constituents forming part of the cosmetic preparations do not always have an adequate stability to light and that they decompose under the effect of the luminous radiations.

It is well known that the most dangerous part of the solar radiation consists of the ultraviolet radiations of wavelengths below 400 nm. It is also known that, because of the existence of the ozone layer in the Earth's atmosphere, which absorbs a proportion of the solar radiation, the lower limit of the ultraviolet radiation reaching the earth's surface lies in the region of 280 nm.

There are already many known compounds capable of absorbing the ultraviolet radiations in the wavelength range from 280 to 320 nm, that is to say in the UV-8 range which plays a dominant role in the production of erythema due to the sun.

Nevertheless, it is also important to have available compounds filtering out the UV-A rays of wavelengths between 320 and 400 nm causing tanning of the skin, but also its aging and promoting the triggering of the erythemateous reaction, or intensifying this reaction in certain individuals or capable of giving rise to phototoxic or photoallergic reactions.

It has already been recommended to employ chalcone derivatives as protective agents capable of absorbing the UV-A rays in order to protect the skin against the harmful effects of the sun. Such chalcone derivatives are described in French Patent Application No. 2,555,167.

However, the production of cosmetic compositions providing protection against the UV rays or of cosmetic compositions stabilized against light requires substances acting as filters in a fairly wide wavelength range and which at the same time are sufficiently soluble in the usual and photostable cosmetic media.

Now, the compounds described in the abovementioned patent application have an insufficient photochemical stability.

The applicant has found that certain derivatives of 2-hydroxychalcone had, surprisingly, good filtering properties in respect of ultraviolet rays, an excellent liposoluble nature, and very good thermal and photochemical stability.

These compounds also offer the advantage of not being toxic or irritant and of being perfectly harmless to the skin.

They distribute themselves uniformly in conventional cosmetic substrates capable of forming a continuous film and particularly in fatty substrates and can therefore be applied to the skin to form an effective protective film.

A subject of the present invention is therefore a cosmetic composition comprising, in a cosmetically acceptable substrate, an effective quantity of at least one derivative of 2-hydroxychalcone having the following general formula:

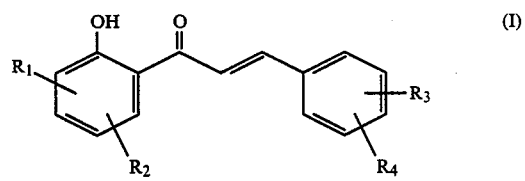

in which $R_1$, $R_2$, $R_3$ and $R_4$ denote, independently of each other, a hydrogen atom, a straight- or branched-chain $C_1$–$C_{12}$ alkyl group, a straight- or branched-chain $C_1$–$C_{12}$ alkoxy group or a straight- or branched-chain $C_2$–$C_{20}$ acyloxy group.

Depending on the nature of the substituents $R_1$, $R_2$, $R_3$ and $R_4$, the compounds of formula (I) absorb the UV radiation between 300 and 400 nm.

Another subject of the present invention is a process for protecting the skin and natural or sensitized hair against solar radiation, consisting in applying to the skin or to the hair an effective quantity of at least one compound of formula (I) contained in a cosmetically acceptable medium.

"Sensitized hair" is understood to mean hair which has undergone a permanent-waving, colouring or bleaching treatment.

Another subject of the invention is a coloured or uncoloured cosmetic composition, stabilized against light, comprising an effective quantity of at least one derivative of 2-hydroxychalcone of formula (I) above.

In the formula (I), above, the straight- or branched-chain $C_1$–$C_{12}$ alkyl group is more particularly a methyl, ethyl, propyl, isopropyl, butyl, isobutyl, tertbutyl or n-hexyl group. The straight- or branched-chain $C_1$–$C_{12}$ alkoxy group more particularly denotes a methoxy, ethoxy, butoxy or hexyloxy group. The straight- or branched-chain $C_2$–$C_{20}$ acyloxy group is more particularly an acetoxy, propionyloxy, butanoyloxy, isobutanoyloxy, tert-butanoyloxy or hexanoyloxy group.

Some of the compounds of the formula (I) are new. The following compounds are involved:
2-hydroxy-4-hexanoyloxy-4'-methoxychalcone
2-hydroxy-4'-hexyloxychalcone
2-hydroxy-3'-hexyloxychalcone and
2-hydroxy-4-hexyloxy-4-methylchalcone.

Compounds of formula (I) which are employed more particularly in the cosmetic composition of the invention are:
2-hydroxychalcone
2-hydroxy-4'-methoxychalcone
2-hydroxy-4'-hexyloxychalcone
2-hydroxy-4'-methylchalcone
2-hydroxy-3'-hexyloxychalcone
2-hydroxy-4-hexyloxy-4'-methylchalcone and 2-hydroxy-4-hexanoyloxy-4′-methoxychalcone.

The 2-hydroxychalcones of formula (I) employed according to the invention are prepared by a process in one or two steps, depending on the meaning of the substituents $R_1$, $R_2$, $R_3$ and $R_4$.

(1) When the substituents $R_1$ to $R_4$ denote a hydrogen atom or an alkyl or alkoxy group, the 2-hydroxychalcones of formula (I) are prepared by a process consisting in reacting an aldehyde of formula (II) with an ortho-hydroxyacetophenone of formula (III) according to the following reaction scheme:

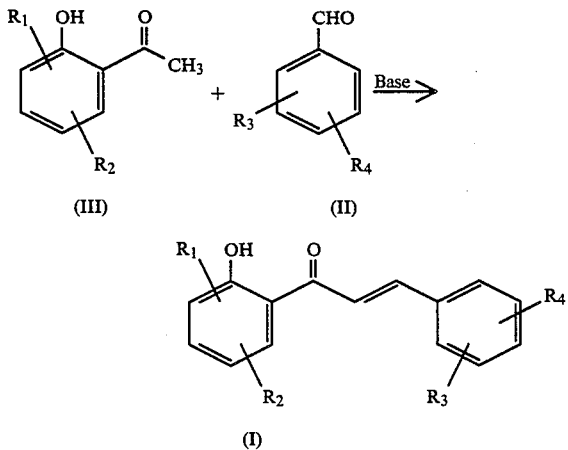

This reaction is carried out in a solvent which may be water, a lower $C_1-C_4$ alcohol or a mixture of water and alcohol, in a basic medium. The alkaline agent is chosen from alkali metal or alkaline-earth metal hydroxides or sodium or potassium alcoholates. The reaction is carried out at a temperature varying between 0° and the boiling temperature of the solvent or of the mixture of solvents.

(2) When one of the substituents $R_1$ to $R_4$ denotes an acyloxy group, the 2-hydroxychalcone of formula (I) is prepared by a two-step process:

(a) the first step consists in reacting an aldehyde of formula (II′) with an ortho-hydroxyacetophenone of formula (III′) according to the following reaction scheme:

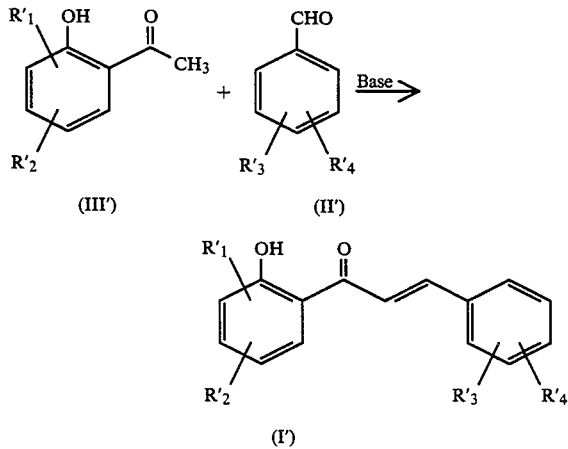

In the compounds of formulae (I′), (II′) and (III′), at least one of the groups $R'_1$ to $R'_4$ denotes a hydroxyl group. The other groups may denote a hydrogen atom, a straight- or branched-chain $C_1-C_{12}$ alkyl group or a straight- or branched-chain $C_1-C_{12}$ alkoxy group.

The operating conditions of this first step are identical with those described for the first process.

(b) The second step consists in performing an acylation reaction of the compound of formula (I′) with an acid chloride or an anhydride of a carboxylic acid containing 2 to 20 carbon atoms according to the following reaction scheme:

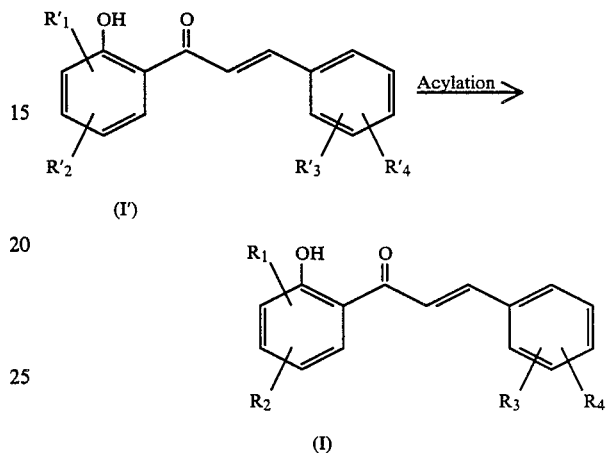

This acylation reaction is carried out in the presence of an organic or inorganic base in a halogenated or aromatic solvent.

The cosmetic composition according to the invention contains 0.5 to 10% by weight, relative to the total weight of the composition, of at least one compound of formula (I) as a protective agent against luminous radiations.

When it is employed as a composition intended to protect human skin against ultraviolet rays, it may be presented in the most diverse forms usually employed for a composition of this type. It may particularly be presented in the form of an oily or oleoalcoholic lotion, an emulsion such as a cream or a milk, an oleoalcoholic or alcoholic gel, a solid stick, or it may be packaged as an aerosol.

It may contain cosmetic adjuvants which are usually employed in a composition of this type, such as thickeners, softeners, humectants, surfactants, preservatives, antifoams, perfumes, oils, waxes, lanolin, propellants, colorants and/or pigments intended to colour the composition itself or the skin, or any other ingredient usually employed in cosmetics.

An oil, a wax and, in general, any fatty substance, a lower monoalcohol or polyalcohol or mixtures thereof may be employed as a solubilizing solvent. The monoalcohols or polyalcohols which are more particularly preferred are ethanol, isopropanol, propylene glycol or glycerine.

An embodiment of the invention is an emulsion in the form of a protective cream or milk comprising, in addition to the compound of formula (I), fatty alcohols, esters of fatty acids and especially fatty acid triglycerides, fatty acids, lanolin, natural or synthetic oils or waxes and emulsifiers, in the presence of water.

Another embodiment consists of oily lotions based on natural or synthetic oils and waxes, lanolin and esters of fatty acids, especially fatty acid triglycerides, or of oleoalcoholic lotions based on a lower alcohol such as ethanol, or a glycol such as propylene glycol and/or a polyol such as glycerine and oils, waxes and fatty acid esters such as fatty acid triglycerides.

The cosmetic composition of the invention may also be an alcoholic gel comprising one or more lower alcohols or polyalcohols such as ethanol, propylene glycol or glycerine and a thickener such as silica. The oleo-alcoholic gels in addition contain an oil or a wax.

The solid sticks consist of natural or synthetic waxes and oils, fatty alcohols, fatty acid esters, lanolin and other fatty substances.

The present invention also relates to the cosmetic sunscreen compositions containing at least one compound of formula (I). The composition may contain other UV-8 and/or UV-A filters.

In this case, the total quantity of filters present in the sunscreen composition is between 0.5 and 10% by weight relative to the total weight of the composition.

By way of solar filters which filter out the UV-8 rays, there may be mentioned water-soluble filters such as the benzylidenecamphor derivatives described in the applicant's French Patents No. 2,199,971, 2,236,515 and 2,383,904 and more particularly 4-(2-oxo-3-bornylidenemethyl)phenyltrimethylammonium methyl sulphate, and the salts of 4-(2-oxo-3-bornylidenemethyl)-benzenesulphonic acid, of 2-methyl-5-(2-oxo-3-bornylidenemethyl)benzenesulphonic acid and of 2-phenyl-benzimidazole-5-sulphonic acid.

The compounds according to the invention may also be combined with UV-B filters consisting of liposoluble compounds or of oils having solar filtering properties such as, especially, coffee oil. By way of lipophilic solar UV-B filters there may be mentioned salicylic acid esters such as 2-ethylhexyl salicylate, homomenthyl salicylate, cinnamic acid esters such as 2-ethylhexyl p-methoxycinnamate and 2-ethoxyethyl p-methoxycinnamate, p-aminobenzoic acid esters such as amyl p-aminobenzoate and 2-ethylhexyl p-dimethylaminobenzoate, benzophenone derivatives such as 2-hydroxy-4-methoxybenzophenone and 2,2'-dihydroxy-4-methoxybenzophenone, camphor derivatives such as 3-(4'-methylbenzylidene)camphor and 3-benzylidenecamphor, and dialkyl benzalmalonates such as di-2-ethylhexyl 4'-methoxybenzalmalonate.

By way of solar filters which filter out the UV-A rays, there may be mentioned dibenzoylmethane derivatives and the derivatives of benzene[di(methylidenecamphor)]sulphonated on the methyl radical in position 10 of camphor, such as are described in French Patent 2,528,420.

It is obvious that the list of solar filters which may be employed in combination with the compounds according to the invention which is indicated above is not limiting.

In the case of a composition packaged as an aerosol, conventional propellants such as alkanes, fluoroalkanes and chlorofluoroalkanes are employed.

When the cosmetic composition according to the invention is intended to protect natural or sensitized hair against UV rays, this composition may be presented in the form of shampoo, lotion, gel or emulsion for rinsing or applying before or after shampooing, before or after colouring or bleaching, before or after permanent-waving, of styling or conditioning lotion or gel, of lotion or gel for blow-drying or hair setting, of hair lacquer, or of a composition for permanent-waving, colouring or bleaching hair. In addition to the compounds of the invention, this composition may contain various adjuvants usually employed in a composition of this type, such as surface-active agents, thickeners, polymers, softeners, preservatives, foam stabilizers, electrolytes, organic solvents, silicon derivatives, oils, waxes, antigrease agents, colorants and/or pigments intended to colour the composition itself or the hair or any other ingredient usually employed in the field of hairdressing.

When the composition forms a shampoo, the latter is essentially characterized in that it contains at least one ionic, nonionic or amphoteric oil-soluble surface agent or a mixture thereof and a compound according to the invention, in an oily medium.

When the composition forms a rinsed emulsion, it is applied before or after colouring or bleaching, before or after permanent-waving, before or after shampooing or between two stages of the shampooing, and is then rinsed off after a period of application.

This composition may be pressurized as an aerosol.

The present invention also provides cosmetic compositions containing at least one compound of formula (I) as an agent for protection against ultraviolet rays, which consist of hairdressing compositions such as hair lacquers, hair setting lotions which may be conditioning or disentangling, shampoos, colouring shampoos, hair-dyeing compositions, of make-up products such as nail varnishes, skin-conditioning creams, foundations, lipsticks, and any other cosmetic composition capable of presenting problems of stability to light during storage owing to its constituents.

The examples which follow are intended to illustrate the invention without, however, being limiting in their nature.

EXAMPLE 1

Preparation of 2-hydroxy-4'-methoxychalcone

A mixture of 3.8 g (0.028 mole) of 2-hydroxyacetophenone, 30 g of potassium hydroxide dissolved in 15 ml of water and 50 ml of ethanol, and 3.8 g (0.028 mole) of anisaldehyde is stirred at ambient temperature for 1 and a half hours. The mixture is then poured into a 10% solution of hydrochloric acid. The precipitate formed is filtered off, washed with water and dried. It is recrystallized from ethanol.

Yield 68%.

Melting point M=94° C.;

UV (CHCl$_3$): wavelength corresponding to the absorption maximum: $\lambda_{max}$=368 nm;

molar extinction coefficient: $\lambda$=27,000

Elemental analysis for C$_{16}$H$_{14}$O$_3$

| Calculated: | C | 75.57; | H | 5.55; | O | 18.87; |
| Found: | C | 75.28 | H | 5.56; | O | 18.82. |

The principal characteristics of other compounds of formula (I) synthesized using the operating procedure described above are summarized in the following table.

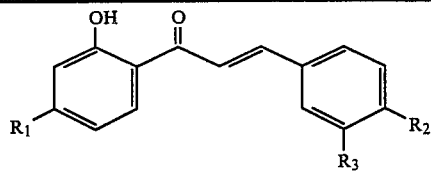

| $R_1$ | $R_2$ | $R_3$ | Yield | Melting point | UV (CHCl$_3$) | Elemental analysis | | Ex. |
|---|---|---|---|---|---|---|---|---|
| H | O—C$_6$H$_{13}$ | H | 47 | 92° | $\lambda$max: 370 nm<br>$\epsilon$: 26300 | (C$_{21}$H$_{24}$O$_3$) Calc.: C: 77.74;<br>H: 7.45; O: 14.79;<br>Found: C: 77.87;<br>H: 7.66; O: 14.48. | | 2 |
| H | CH$_3$ | H | 64 | 120° | $\lambda$max: 335 nm<br>$\epsilon$: 22400 | (C$_{16}$H$_{14}$O$_2$) Calc.: C: 80.65;<br>H: 5.92; O: 13.43;<br>Found: C: 80.38;<br>H: 5.94; | O: 13.27. | 3 |
| H | H | O—C$_6$H$_{13}$ | 33 | <50° | $\lambda$max$_1$: 314 nm<br>$\epsilon_1$: 17900<br>$\lambda$max$_2$: 354 nm<br>$\epsilon_2$: 15200 | (C$_{21}$H$_{24}$O$_3$) Calc.: C: 77.74;<br>H: 7.45; O: 14.79;<br>Found: C: 77.84;<br>H: 7.48; O: 14.83. | | 4 |
| O—C$_6$H$_{13}$ | CH$_3$ | H | 35 | 90° | $\lambda$max: 357 nm<br>$\epsilon$: 27780 | (C$_{22}$H$_{26}$O$_3$) Calc.: C: 78.07;<br>H: 7.74; O: 14.18;<br>Found: C: 77.93;<br>H: 7.77; O: 14.14 | | 5 |
| H | H | H | 78 | 94° | $\lambda$max: 318 nm<br>$\epsilon$: 21400 | (C$_{15}$H$_{12}$O$_2$) Calc.: C: 80.33;<br>H: 5.39; O: 14.27;<br>Found: C: 80.55;<br>H: 5.46; O: 14.25. | | 6 |

EXAMPLE 7

(1) Preparation of 2,4-dihydroxy-4'-methoxychalcone

A mixture of 3.04 g (0.02 mole) of 2,4-dihydroxyacetophenone, 10 ml of 60% strength aqueous potassium hydroxide and 10 ml of ethanol is cooled to 0° C. 2.72 g (0.02 mole) of anisaldehyde are added with stirring and the reaction mixture is heated to 50° C. for 4 hours. The mixture is then poured into a 10% solution of hydrochloric acid. The precipitate formed is filtered off, washed three times with water and is dried. It is then taken up with ethyl acetate, is treated with animal charcoal and is filtered rapidly through silica with a 9/1 mixture of pentane and ethyl acetate. A yellow product is obtained.

Yield: 31%; melting point M=194° C.

(2) Preparation of 2-hydroxy-4-hexanoyloxy-4'-methoxychalcone by acylation of 2,4-dihydroxy-4'-methoxychalcone A mixture of 1.35 g (0.005 mole) of 2,4-dihydroxy-4'-methoxychalcone, 0.79 g (0.01 mole) of pyridine, 15 ml of dichloromethane and 0.67 g (0.005 mole) of hexanoyl chloride is heated under reflux for 2 hours. The reaction mixture is then poured into a 10% solution of hydrochloric acid and is extracted with dichloromethane. The organic phase is washed with water, with a 5% solution of sodium bicarbonate and then with water. It is dried and evaporated to dryness; the residue obtained is filtered rapidly through silica with a mixture of pentane and ethyl acetate (9/1). A yellow product is obtained.

Yield: 62%

Melting point M=78° C. UV (CHCl$_3$): $\lambda_{max}$: 368 nm; $\epsilon$=31,000

Elemental analysis for C$_{22}$H$_{24}$O$_5$

| Calculated: | C | 71.71; | H | 6.56; | O | 21.71; |
|---|---|---|---|---|---|---|

-continued

| Found: | C | 71.83; | H | 6.66; | O | 21.55. |
|---|---|---|---|---|---|---|

EXAMPLES OF APPLICATION

Example 1—Sun milk

| | |
|---|---|
| Compound of Example 4 | 4 g |
| Mixture of esters of fatty acids, of polyglycerolated esters and of silicone surfactant sold under the name of "Abil WS 08" by Goldschmidt | 5 g |
| Benzoate of C$_{12}$—C$_{15}$ alcohols sold under the name of "Finsolv TN" by Witco | 15 g |
| Cyclotetradimethylsiloxane | 4 g |
| Vaseline | 2 g |
| Beeswax and cetostearyl palmitostearate | 2.5 g |
| Glycerine | 5 g |
| Sodium chloride | 2 g |
| Perfume, preservatives q.s. | |
| Water q.s. | 100 g |

The product is a water-in-oil emulsion.

It is prepared in a conventional manner by dissolving the filter in the fatty substances and the emulsifiers, by heating this fatty phase to about 75°–80° C. and by adding, with vigorous stirring, water and glycerine, both also heated to 75°–80° C. Stirring is continued for 10 to 15 minutes and then the mixture is allowed to cool with moderate stirring and perfume and preservatives are added to about 40° C.

Example 2—Sun oil

The following ingredients are mixed by heating if appropriate to 40°–45° C. in order to homogenize:

| | |
|---|---|
| Compound of Example 4 | 2.5 g |
| Benzoate of C$_{12}$—C$_{15}$ alcohols sold under the name of "Finsolv TN" by Witco | 30 g |
| Triglycerides of oleic and linoleic acids | 20 g |

9

-continued

| | |
|---|---|
| Antioxidants, perfume q.s. | |
| Cyclotetradimethylsiloxane q.s. | 100 g |

Example 3—Protective day cream

| | |
|---|---|
| Compound of Example 2 | 2 g |
| Mixture of alcohols: cetylstearyl and cetyl-stearyl oxyethylenated with 33 moles of ethylene oxide | 7 g |
| Mixture of glycerol mono- and distearate | 2 g |
| Cetyl alcohol | 1.5 g |
| Modified polydimethylsiloxane | 0.1 g |
| "Finsolv TN" | 20 g |
| Glycerine | 15 g |
| Perfume, preservatives q.s. | |
| Water q.s. | 100 g |

The product is an oil-in-water emulsion.

The filter is dissolved in the fatty substances and these are heated to 70°–80° C.; the aqueous phase consisting of water, glycerine and the emulsifiers is heated to the same temperature, the fatty phase is added to the aqueous phase with vigorous stirring. Stirring is continued for 10 to 15 minutes, then the mixture is allowed to cool with moderate stirring and perfume and preservatives are added at about 40° C.

Example 4—Solid stick

| | |
|---|---|
| Compound of Example 4 | 2.5 g |
| Mixture of beeswax and of cetostearyl palmitostearate | 7 g |
| Hydrocarbon mineral wax | 20 g |
| Oleyl alcohol | 12 g |
| Hydrogenated lanolin | 8 g |
| Liquid lanolin | 8 g |
| Carnauba wax | 1 g |
| "Finsolv TN" | 20 g |
| Antioxidants, perfume q.s. | |
| Liquid paraffin q.s. | 100 g |

Example 5—Sun cream

| | |
|---|---|
| Compound of Example 4 | 5 g |
| Mixture of alcohols: cetylstearyl and cetylstearyl oxyethylenated with 33 moles of ethylene oxide | 7 g |
| Mixture of glycerol mono- and distearate | 2 g |
| Cetyl alcohol | 1.5 g |
| "Finsolv TN" | 20 g |
| Modified polydimethylsiloxane | 0.1 g |
| Glycerine | 15 g |
| Perfume, preservatives q.s. | |
| Water q.s. | 100 g |

The product is an oil-in-water emulsion which is obtained in the same manner as in Example 3.

Example 6—Sun oil

| | |
|---|---|
| Compound of Example 4 | 2 g |
| 2-Ethylhexyl p-methoxycinnamate | 2 g |
| Benzoate of $C_{12}$—$C_{15}$ alcohols sold under the name of "Finsolv TN" by Witco | 30 g |
| Triglycerides of oleic and linoleic acids | 20 g |
| Antioxidants, perfume q.s. | |
| Cyclotetradimethylsiloxane q.s. | 100 g |

10

This oil is prepared in the same manner as that of Example 2.

Example 7—Sun milk

| | |
|---|---|
| Compound of Example 4 | 3 g |
| Di-2-ethylhexyl 4'-methoxybenzalmalonate | 4 g |
| Benzoate of $C_{12}$—$C_{15}$ alcohols sold under the name of "Finsolv TN" by Witco | 15 g |
| Cyclotetradimethylsiloxane | 4 g |
| Vaseline | 2 g |
| Beeswax and cetostearyl palmitostearate | 2.5 g |
| Glycerine | 5 g |
| Sodium chloride | 2 g |
| Perfume, preservatives q.s. | |
| Water q.s. | 100 g |

The product is a water-in-oil emulsion, prepared in the same manner as that in Example 1.

Example 8—Sun stick

| | |
|---|---|
| Compound of Example 2 | 1.5 g |
| 3-(4'-Methylbenzylidene)camphor | 1.5 g |
| Mineral hydrocarbon wax | 20 g |
| Mixture of beeswax and of cetostearyl palmitostearate | 7 g |
| Oleyl alcohol | 12 g |
| Hydrogenated lanolin | 8 g |
| Liquid lanolin | 8 g |
| Carnauba wax | 1 g |
| Benzoate of $C_{12}$—$C_{15}$ alcohols sold under the name of "Finsolv TN" by Witco | 20 g |
| Antioxidants, perfume q.s. | |
| Liquid paraffin q.s. | 100 g |

This solid stick is prepared by heating the various constituents to about 80° C. to obtain a liquid phase in which the filters are dissolved and then the mass is allowed to return to ambient temperature.

We claim:

1. Filtering cosmetic composition for protecting the skin and the hair against ultraviolet rays, which comprises, in a cosmetically acceptable substrate, as a compound filtering out the ultraviolet radiation of wavelengths between 300 and 400 nm, an effective quantity of at least one 2-hydroxychalcone compound of the formula:

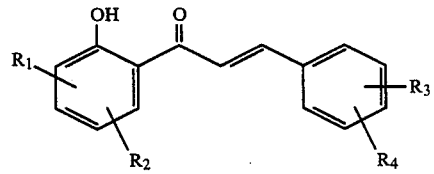

in which $R_1$, $R_2$, $R_3$ and $R_4$ denote, independently of each other, a hydrogen atom, a straight- or branched-chain $C_1$–$C_{12}$ alkyl group, a straight- or branched-chain $C_1$–$C_{12}$ alkoxy group or a straight- or branched-chain $C_2$–$C_{20}$ acyloxy group.

2. Cosmetic composition according to claim 1, which comprises, as a compound of the formula of claim 1, at least one compound selected from the group consisting of 2-hydroxychalcone, 2-hydroxy-4'-methoxychalcone, 2-hydroxy-4'-hexyloxychalcone, 2-hydroxy-4'-methylchalcone, 2-hydroxy-3'-hexyloxychalcone, 2-hydroxy-4-hexyloxy-4'-methylchalcone and 2-hydroxy-4-hexanoyloxy-4'-methoxychalcone.

3. Cosmetic composition according to claim 1 which comprises from 0.5 to 10 % by weight, relative to the total weight of the composition, of one or more compounds of 2-hydroxychalcone of the formula of claim 1.

4. Cosmetic composition according to claim 1, intended to be applied to the skin, which is in the form of an oily or oleoalcoholic lotion, an emulsion, an oleoalcoholic or alcoholic gel, a solid stick or an aerosol.

5. Cosmetic composition according to claim 4, which additionally contains cosmetic adjuvants selected from the group consisting of thickeners, softeners, humectants, surfactants, preservatives, antifoams, perfumes, oils, waxes, lanolin, lower monoalcohols and polyalcohols, propellants, colorants and pigments.

6. Cosmetic composition according to claim 4, which is presented in the form of a sunscreen composition, which additionally contains an agent filtering out the UV-B or UV-A rays.

7. Cosmetic composition according to claim 6, wherein the UV-B filter is selected from the group consisting of 4-(2-oxo-3-bornylidenemethyl)phenyltrimethylammonium methyl sulphate, salts of 4-(2-oxobornylidenemethyl)benzenesulphonic acid, of 2-methyl-5-(2-oxo-3-bornylidenemethyl)benzenesulphonic acid and of 2-phenylbenzimidazole-5-sulphonic acid, coffee oil, salicylic acid esters, cinnamic acid esters, p-aminobenzoic acid esters, benzophenone derivatives, 3-benzylidenecamphor, 3-(4'-methylbenzylidene) camphor and dialkyl benzalmalonates.

8. Cosmetic composition according to claim 6, wherein the UV-A filter is chosen from dibenzoylmethane derivatives and the derivatives of benzene[di(methylidenecamphor)]sulphonated on the methyl radical in position 10 of camphor.

9. Cosmetic composition according to claim 1, which additionally contains at least one cosmetic adjuvant selected from the group consisting of surface-active agents, thickeners, polymers, softeners, preservatives, foam stabilizers, electrolytes, organic solvents, silicone derivatives, oils, waxes, antigrease agents, colorants and pigments.

10. Process for protecting the skin and the hair against ultraviolet radiation, which consists in applying to the skin or the hair an effective quantity of a cosmetic composition containing at least one derivative of 2-hydroxychalcone of formula (I) according to claim 1.

* * * * *